US011524691B2

(12) United States Patent
Gallagher et al.

(10) Patent No.: US 11,524,691 B2
(45) Date of Patent: Dec. 13, 2022

(54) SYSTEM AND METHOD FOR CONTROLLING AN INTERIOR ENVIRONMENTAL CONDITION IN A VEHICLE

(71) Applicant: Lear Corporation, Southfield, MI (US)

(72) Inventors: David Gallagher, Sterling Heights, MI (US); Francesco Migneco, Saline, MI (US); Marie-Eve Cote, Royal Oak, MI (US); Vyachislav Ivanov, West Bloomfield, MI (US); Karl Henn, New Hudson, MI (US); Michael R. Powell, Waterford, MI (US)

(73) Assignee: LEAR Corporation, Southfield, MI (US)

( * ) Notice: Subject to any disclaimer, the term of this patent is extended or adjusted under 35 U.S.C. 154(b) by 160 days.

(21) Appl. No.: 16/524,865

(22) Filed: Jul. 29, 2019

(65) Prior Publication Data
US 2021/0031786 A1  Feb. 4, 2021

(51) Int. Cl.
  *B60W 50/00* (2006.01)
  *B60H 1/00* (2006.01)
  (Continued)

(52) U.S. Cl.
  CPC ..... *B60W 50/0098* (2013.01); *A61B 5/02055* (2013.01); *A61B 5/6893* (2013.01);
  (Continued)

(58) Field of Classification Search
  CPC ......... B60W 50/0098; B60W 2552/00; B60W 2554/00; B60W 2555/20; B60W 2556/45;
  (Continued)

(56) References Cited

U.S. PATENT DOCUMENTS 5,694,939 A  12/1997 Cowings
5,807,114 A   9/1998 Hodges et al.
(Continued)

FOREIGN PATENT DOCUMENTS

CN  102254403 A  11/2011
CN  103043057 A   4/2013
(Continued)

OTHER PUBLICATIONS

Migneco, Francesco et al., Amendment Under 37 C.F.R. § 1.111 for U.S. Appl. No. 15/808,325 filed with the U.S. Patent and Trademark Office on Jul. 10, 2020 (10 Pages).
(Continued)

*Primary Examiner* — Peter D Nolan
*Assistant Examiner* — Peter Y Ning
(74) *Attorney, Agent, or Firm* — Brooks Kushman P.C.

(57) ABSTRACT

A system and method are described for controlling a vehicle interior environmental condition. A biometric sensor senses a biometric condition of a vehicle seat occupant and generates a sensed biometric condition value. A controller receives the sensed biometric condition value, a sensed interior environmental condition value, and a sensed exterior environmental condition value. Each of multiple exterior environmental condition values has an associated biometric condition value defined as optimal for the vehicle occupant. The controller determines the optimal biometric condition value associated with the sensed exterior environmental condition value, compares the optimal biometric condition value to the sensed biometric condition value, and in response to a difference between the optimal biometric condition value and the sensed biometric condition value, generates a control signal to control an actuator to control the controllable interior environmental condition to reduce
(Continued)

the difference between sensed biometric condition value and the optimal biometric condition value.

20 Claims, 8 Drawing Sheets

(51) Int. Cl.
| | |
|---|---|
| *B60Q 3/80* | (2017.01) |
| *A61B 5/0205* | (2006.01) |
| *A61B 5/00* | (2006.01) |
| *G05B 13/02* | (2006.01) |
| *B60N 2/02* | (2006.01) |
| *A61B 5/08* | (2006.01) |
| *A61B 5/02* | (2006.01) |
| *A61B 5/021* | (2006.01) |
| *A61B 5/053* | (2021.01) |
| *A61B 5/145* | (2006.01) |
| *A61B 5/11* | (2006.01) |
| *A61B 5/369* | (2021.01) |

(52) U.S. Cl.
CPC ....... *A61B 5/7267* (2013.01); *B60H 1/00742* (2013.01); *B60H 1/00821* (2013.01); *B60H 1/00964* (2013.01); *B60N 2/0244* (2013.01); *B60Q 3/80* (2017.02); *G05B 13/0265* (2013.01); *A61B 5/021* (2013.01); *A61B 5/02035* (2013.01); *A61B 5/053* (2013.01); *A61B 5/08* (2013.01); *A61B 5/1118* (2013.01); *A61B 5/14542* (2013.01); *A61B 5/369* (2021.01); *A61B 5/4266* (2013.01); *B60W 2540/22* (2013.01); *B60W 2552/00* (2020.02); *B60W 2554/00* (2020.02); *B60W 2555/20* (2020.02); *B60W 2556/45* (2020.02)

(58) Field of Classification Search
CPC ........... B60W 2540/22; B60H 1/00742; B60H 1/00964; B60H 1/00821; B60Q 3/80; A61B 5/02055; A61B 5/6893; A61B 5/7267; A61B 5/369; A61B 5/08; A61B 5/02035; A61B 5/021; A61B 5/053; A61B 5/14542; A61B 5/4266; A61B 5/1118; B60N 2/0244
See application file for complete search history.

(56) References Cited

U.S. PATENT DOCUMENTS

| | | | |
|---|---|---|---|
| 6,366,207 B1 | 4/2002 | Murphy | |
| 6,438,399 B1 | 8/2002 | Kurth | |
| 7,138,922 B2 | 11/2006 | Strumolo et al. | |
| 7,431,120 B2* | 10/2008 | Pollehn | G08B 21/06 |
| | | | 180/272 |
| 7,437,219 B2 | 10/2008 | Bos | |
| 7,774,052 B2 | 8/2010 | Burton et al. | |
| 8,698,639 B2 | 4/2014 | Fung et al. | |
| 8,706,204 B2 | 4/2014 | Seo et al. | |
| 8,903,494 B2 | 12/2014 | Goldwasser et al. | |
| 8,941,499 B2 | 1/2015 | Fung et al. | |
| 9,002,458 B2 | 4/2015 | Pal et al. | |
| 9,014,811 B2 | 4/2015 | Pal et al. | |
| 9,124,955 B2 | 9/2015 | Geva et al. | |
| 9,135,803 B1 | 9/2015 | Fields et al. | |
| 9,149,236 B2 | 10/2015 | Chun et al. | |
| 9,159,232 B2* | 10/2015 | Ricci | B60W 40/09 |
| 9,233,244 B2 | 1/2016 | Pal et al. | |
| 9,272,689 B2 | 3/2016 | Fung et al. | |
| 9,298,985 B2 | 3/2016 | Krueger | |
| 9,302,584 B2 | 4/2016 | Walsh et al. | |
| 9,389,595 B2 | 7/2016 | Caskey et al. | |
| 9,440,646 B2 | 9/2016 | Fung et al. | |
| 9,454,887 B1 | 9/2016 | Matalgah | |
| 9,460,601 B2 | 10/2016 | Mimar | |
| 9,463,794 B1 | 10/2016 | Silver et al. | |
| 9,475,502 B2 | 10/2016 | Fung et al. | |
| 9,536,411 B2 | 1/2017 | Foley et al. | |
| 9,539,944 B2 | 1/2017 | Tzirkel-Hancock et al. | |
| 9,712,736 B2 | 7/2017 | Kearns et al. | |
| 9,848,814 B2 | 12/2017 | Benson et al. | |
| 9,956,963 B2 | 5/2018 | Vijaya Kumar et al. | |
| 10,054,443 B1 | 8/2018 | Patel et al. | |
| 10,210,409 B1 | 2/2019 | Migneco et al. | |
| 10,246,102 B2* | 4/2019 | Graney | B60K 35/00 |
| 10,379,535 B2 | 8/2019 | Migneco et al. | |
| 10,425,459 B2 | 9/2019 | Rider et al. | |
| 10,836,403 B2 | 11/2020 | Migneco et al. | |
| 10,867,218 B2 | 12/2020 | Gallagher et al. | |
| 2005/0022606 A1 | 2/2005 | Partin et al. | |
| 2005/0131607 A1* | 6/2005 | Breed | B60N 2/002 |
| | | | 701/45 |
| 2006/0015000 A1 | 1/2006 | Kim | |
| 2007/0156295 A1 | 7/2007 | Stephane | |
| 2008/0252466 A1 | 10/2008 | Yopp et al. | |
| 2009/0174573 A1 | 7/2009 | Smith | |
| 2009/0268022 A1 | 10/2009 | Omi | |
| 2012/0116198 A1 | 5/2012 | Veen et al. | |
| 2012/0150430 A1 | 6/2012 | French et al. | |
| 2012/0259181 A1 | 10/2012 | Fujita et al. | |
| 2012/0265262 A1 | 10/2012 | Osorio | |
| 2012/0330173 A1 | 12/2012 | Park et al. | |
| 2013/0054090 A1 | 2/2013 | Shin et al. | |
| 2013/0088369 A1 | 4/2013 | Yu et al. | |
| 2013/0204153 A1 | 8/2013 | Buzhardt | |
| 2013/0325202 A1 | 12/2013 | Howard et al. | |
| 2014/0136450 A1 | 5/2014 | Lee | |
| 2014/0139655 A1 | 5/2014 | Mimar | |
| 2014/0221781 A1 | 8/2014 | Schrauf et al. | |
| 2015/0008710 A1 | 1/2015 | Young et al. | |
| 2015/0032382 A1 | 1/2015 | Lee et al. | |
| 2015/0245777 A1 | 9/2015 | Della Torre et al. | |
| 2015/0313475 A1 | 11/2015 | Benson et al. | |
| 2015/0328985 A1 | 11/2015 | Kim et al. | |
| 2015/0360608 A1 | 12/2015 | Tzirkel-Hancock et al. | |
| 2015/0379362 A1 | 12/2015 | Calmes et al. | |
| 2016/0001781 A1 | 1/2016 | Fung et al. | |
| 2016/0090097 A1 | 3/2016 | Grube et al. | |
| 2016/0133151 A1 | 5/2016 | O'Dowd et al. | |
| 2016/0260343 A1 | 9/2016 | Resl | |
| 2016/0285938 A1 | 9/2016 | Rider et al. | |
| 2016/0292988 A1 | 10/2016 | McCleary et al. | |
| 2016/0354027 A1 | 12/2016 | Benson et al. | |
| 2016/0362118 A1 | 12/2016 | Mollicone et al. | |
| 2016/0378112 A1 | 12/2016 | Ljubuncic et al. | |
| 2017/0068245 A1 | 3/2017 | Scofield et al. | |
| 2017/0071525 A1 | 3/2017 | Lin et al. | |
| 2017/0083757 A1 | 3/2017 | Enomoto et al. | |
| 2017/0136842 A1 | 5/2017 | Anderson et al. | |
| 2017/0188927 A1 | 7/2017 | Nakashima et al. | |
| 2017/0196497 A1 | 7/2017 | Ray et al. | |
| 2017/0267170 A1 | 9/2017 | Be et al. | |
| 2017/0278122 A1 | 9/2017 | Kaehler | |
| 2017/0311831 A1 | 11/2017 | Freer et al. | |
| 2017/0349061 A1 | 12/2017 | Benson et al. | |
| 2017/0351812 A1 | 12/2017 | Green et al. | |
| 2017/0355377 A1 | 12/2017 | Vijaya Kumar et al. | |
| 2017/0360363 A1 | 12/2017 | Fonseca et al. | |
| 2017/0367635 A1 | 12/2017 | Hur et al. | |
| 2017/0367651 A1 | 12/2017 | Tzvieli | |
| 2017/0370732 A1 | 12/2017 | Bender et al. | |
| 2018/0008145 A1 | 1/2018 | Freer et al. | |
| 2018/0065642 A1 | 3/2018 | Frye et al. | |
| 2018/0136191 A1 | 5/2018 | Advadi et al. | |
| 2018/0143006 A1 | 5/2018 | White | |
| 2018/0189681 A1 | 7/2018 | Harrivel et al. | |
| 2018/0197636 A1 | 7/2018 | Firminger et al. | |
| 2018/0229674 A1* | 8/2018 | Heinrich | B60K 28/063 |
| 2018/0263545 A1 | 9/2018 | Camporesi et al. | |
| 2018/0276362 A1 | 9/2018 | Baughman et al. | |
| 2018/0333093 A1 | 11/2018 | Gallagher et al. | |
| 2018/0348740 A1* | 12/2018 | Rocci | G06V 20/597 |

(56) References Cited

U.S. PATENT DOCUMENTS

| | | | |
|---|---|---|---|
| 2019/0038229 | A1 | 2/2019 | Perraut et al. |
| 2019/0049942 | A1 | 2/2019 | Dusane |
| 2019/0049968 | A1 | 2/2019 | Dean et al. |
| 2019/0087691 | A1 | 3/2019 | Jelveh |
| 2019/0108407 | A1 | 4/2019 | Okayasu |
| 2019/0133511 | A1 | 5/2019 | Migneco et al. |
| 2019/0168771 | A1 | 6/2019 | Migneco et al. |
| 2019/0176837 | A1 | 6/2019 | Williams et al. |
| 2019/0184853 | A1 | 6/2019 | Thomas et al. |
| 2019/0193712 | A1* | 6/2019 | Kusanagi ............... B60Q 3/80 |
| 2019/0332902 | A1 | 10/2019 | Gallagher et al. |
| 2019/0346843 | A1 | 11/2019 | Stark et al. |
| 2019/0373038 | A1 | 12/2019 | Rider et al. |
| 2019/0373114 | A1 | 12/2019 | Gullander |
| 2020/0012403 | A1 | 1/2020 | Sculley et al. |
| 2020/0062074 | A1* | 2/2020 | Macneille ........ B60H 1/00735 |
| 2020/0155054 | A1* | 5/2020 | Slater ..................... A61B 5/08 |
| 2020/0398700 | A1 | 12/2020 | Migneco et al. |
| 2021/0009149 | A1 | 1/2021 | Migneco et al. |

FOREIGN PATENT DOCUMENTS

| | | |
|---|---|---|
| CN | 103198617 A | 7/2013 |
| CN | 204147427 U | 2/2015 |
| CN | 104700572 A | 6/2015 |
| CN | 105595996 A | 5/2016 |
| CN | 106687026 A | 5/2017 |
| CN | 107791893 A | 3/2018 |
| CN | 107949504 A | 4/2018 |
| CN | 108937883 A | 12/2018 |
| CN | 109843174 A | 6/2019 |
| CN | 109927603 A | 6/2019 |
| DE | 10126224 A1 | 12/2002 |
| DE | 102012002037 B4 | 3/2015 |
| EP | 2308559 A2 | 4/2011 |
| FR | 2880166 A1 | 6/2006 |
| JP | 2010241963 A | 10/2010 |
| JP | 2017021651 A | 1/2017 |
| JP | 2017042544 A | 3/2017 |
| WO | 2007090896 A1 | 8/2007 |
| WO | 2015127193 A1 | 8/2015 |
| WO | 2015175435 A1 | 11/2015 |

OTHER PUBLICATIONS

Migneco, Francesco et al., Preliminary Amendment for U.S. Appl. No. 15/830,892, filed with the U.S. Patent and Trademark Office on Sep. 23, 2019 (9 Pages).

Gallagher, David et al., Preliminary Amendment for U.S. Appl. No. 15/963,697, filed with the U.S. Patent and Trademark Office on Jan. 15, 2020 (8 Pages).

Migneco, Francesco et al., Amendment Under 37 C.F.R. § 1.111 for U.S. Appl. No. 15/808,325, filed with the U.S. Patent and Trademark Office on Jan. 9, 2020 (10 Pages).

Burgess, M., "This car headrest monitors your brain waves to stop you falling asleep at the wheel", Wired Online Article, Jan. 15, 2017, 9 pgs.

Wess, J., "Prototype Testing of EEG Headrests", Freer Logic Online Article—Comments on Prototype Testing of EEG Headrests, Aug. 3, 2017, 2 pgs.

Lisetti, C., "Affective Intelligent Car Interfaces with Emotion Recognition", In Proceedings of 11th International Conference on Human Computer Interaction, Las Vegas, NV, USA, Jul. 2005.

Stout, Cynthia S., et al., Increasing Accuracy in the Assessment of Motion Sickness: A Construct Methodology, Ames Research Center, NASA Technical Memorandum 108797, Dec. 1993, Moffett Field, California.

Migneco, Francesco et al., Amendment Under 37 C.F.R. § 1.111 for U.S. Appl. No. 15/830,892 filed with the U.S. Patent and Trademark Office on Jun. 17, 2020 (7 Pages).

Gallagher, David et al., Supplemental Amendment Under 37 C.F.R. § 1.111 for U.S. Appl. No. 15/963,697 filed with the U.S. Patent and Trademark Office on Jun. 2, 2020 (12 Pages).

Gallagher, David, et al., Amendment Under 37 C.F.R. §1.116 for U.S. Appl. No. 15/963,697 filed with the U.S. Patent and Trademark Office on Sep. 8, 2020 (8 pages).

The State Intellectual Property Office of the People's Republic of China, First Office Action for Chinese Patent Application No. 201811467580.X, dated Jul. 28, 2021, 11 Pages.

"Shaffer et al., ""An Overview of Heart Rate Variability Metrics and Norms,"" published online Sep. 28, 2017, 51 pages, <<https://www.ncbi.nlm.nih.gov/pmc/articles/PMC5624990>>."

Migneco, Francesco et al., Preliminary Amendment for U.S. Appl. No. 16/448,306, filed with the U.S. Patent and Trademark Office on May 7, 2020 (7 Pages).

Migneco, Francesco et al., Reply Under 37 C.F.R. § 1.111 for U.S. Appl. No. 16/448,306 filed with the U.S. Patent and Trademark Office on Jun. 2, 2022 (11 Pages).

Migneco, Francesco et al., Amendment Under 37 C.F.R. § 1.111 for U.S. Appl. No. 17/033,383, filed with the U.S. Patent and Trademark Office on Jul. 21, 2022 (7 Pages).

Migneco, Francesco et al., Preliminary Amendment for U.S. Appl. No. 17/033,383, filed with the U.S. Patent and Trademark Office on Sep. 25, 2020 (3 Pages).

Migneco, Francesco et al., Supplemental Preliminary Amendment for U.S. Appl. No. 17/033,383, filed with the U.S. Patent and Trademark Office on Oct. 20, 2020 (7 Pages).

U.S. Appl. No. 15/830,892, filed Dec. 4, 2017.
U.S. Appl. No. 15/808,325, filed Nov. 9, 2017.
U.S. Appl. No. 15/963,697, filed Apr. 26, 2018.

\* cited by examiner

SYSTEM AND METHOD FOR CONTROLLING AN INTERIOR ENVIRONMENTAL CONDITION IN A VEHICLE

TECHNICAL FIELD

The following relates to a system and method for controlling an interior environmental condition in a vehicle.

BACKGROUND

Automobile users often overcompensate conscious changes to vehicle system inputs as a means of correcting or adjusting their autonomic functions relating to physiological and/or phycological status. For example, a user experiencing and/or perceiving an uncomfortably low ambient air temperature in a vehicle cabin may overcompensate by adjusting a vehicle cabin temperature setting to a level intended to correct the experience or perception of the uncomfortably low ambient air temperature, but which ultimately results in an ambient air temperature that the user experiences and/or perceives as uncomfortably high and that necessitates further adjustment by the user of the vehicle cabin temperature setting.

Moreover, interest in the automotive industry in intuitive human-machine interfaces (HMI), user systems, and memory-based occupant settings is high. In that regard, both vehicle original equipment manufacturers (OEM) and end user customers seek a dynamic, automatic, and seamless user experience, which can be a primary basis for quality perception.

A need therefore exists for a system and method capable of automatically monitoring user autonomic functions and setting and/or adjusting vehicle conditions accordingly. Such a system and method would provide for integration of neuro-monitoring (e.g., electro-encephalogram (EEG)) with other user biometrics and which may utilize a long-term machine learning algorithm to provide for objective assessments that may be combined with subjective trends and both internal and external vehicle conditions. Such a system and method would automatically adjust vehicle conditions to put an occupant in the best scenarios based not on generalized case study data but also upon the occupant's own biometric inputs, surrounding conditions, and a continuously learning machine, thereby creating a highly personalized user experience in vehicle.

A system and method capable of monitoring, learning, and reacting in such a fashion would mitigate the problem of user over reaction or overcompensation described above. Such a system and method would also enable creation of a customized user profile, which could be dynamic. Such a user profile could also be shared so that other vehicle systems beyond the user's own vehicle systems would be able not only adjust to the user but also continue to learn and customize to the user.

Improving vehicle conditions to positively benefit occupant autonomic function (e.g., stress, drowsiness, etc.) would provide considerable short-term and long-term health and safety benefits. Moreover, the ability to not only transmit but receive data from multiple seat locations and vehicles to share and update information would improve user quality perception and user experience. Such a system design and method may also be particularly useful in fully autonomous vehicles.

SUMMARY

According to one non-limiting exemplary embodiment described herein, a system is provided for controlling an interior environmental condition in a vehicle. The system comprises a biometric sensor configured to sense a biometric condition of an occupant of the seat and generate a signal representative of a value of the sensed biometric condition, and a controller configured to receive the biometric condition signal, an interior environmental condition signal representative of a value of a sensed controllable interior environmental condition, and an exterior environmental condition signal representative of a value of a sensed exterior environmental condition. Each of a plurality of exterior environmental condition values has associated therewith a biometric condition value defined as an optimal biometric condition value for the vehicle occupant for the corresponding exterior environmental condition value. The controller is configured to determine the optimal biometric condition value for the vehicle occupant associated with the sensed exterior environmental condition value, compare the optimal biometric condition value for the vehicle occupant to the sensed biometric condition value, and in response to a difference between the optimal biometric condition value and the sensed biometric condition value, generate a control signal to control an actuator configured to control the controllable interior environmental condition. The control signal effectuates control of the actuator to reduce the difference between the sensed biometric condition value and the optimal biometric condition value.

According to another non-limiting exemplary embodiment described herein, a method is provided for controlling an interior environmental condition in a vehicle. The method comprises sensing a biometric condition of an occupant of a vehicle seat and generating a signal representative of a value of the sensed biometric condition, sensing a controllable interior environmental condition in the vehicle and generating a signal representative of a value of the sensed interior environmental condition, and sensing an environmental condition exterior to the vehicle and generating a signal representative of a value of the sensed exterior environmental condition. Each of a plurality of exterior environmental condition values has associated therewith a biometric condition value defined as an optimal biometric condition value for the occupant for the corresponding exterior environmental condition value. The method further comprises determining the optimal biometric condition value for the occupant associated with the sensed exterior environmental condition value, comparing the optimal biometric condition value for the occupant to the sensed biometric condition value, and in response to a difference between the optimal biometric condition value and the sensed biometric condition value, generating a control signal to control an actuator configured to control the controllable interior environmental condition. The control signal effectuates control of the actuator to reduce the difference between the optimal biometric condition value and the sensed biometric condition value.

According to yet another non-limiting exemplary embodiment described herein, a non-transitory computer readable storage medium is provided having stored computer executable instructions for controlling an interior environmental condition in a vehicle comprising a biometric sensor configured to sense a biometric condition of an occupant of a vehicle seat and generate a signal representative of a value of the sensed biometric condition, a vehicle interior sensor configured to sense a controllable interior environmental condition in the vehicle and generate a signal representative of a value of the sensed interior environmental condition, a vehicle exterior sensor configured to sense an environmental condition exterior to the vehicle and generate a signal representative of a value of the sensed exterior environmental condition, wherein a controller is configured to receive the biometric condition signal, the interior environmental condition signal, and the exterior environmental condition signal, wherein each of a plurality of exterior environmental condition values has associated therewith a biometric condition value defined as an optimal biometric condition value for the occupant for the corresponding exterior environmental condition value. The computer executable instructions configured to cause the controller to determine the optimal biometric condition value for the occupant associated with the sensed exterior environmental condition value, compare the optimal biometric condition value for the occupant to the sensed biometric condition value, and in response to a difference between the optimal biometric condition value and the sensed biometric condition value, generate a control signal to control an actuator configured to control the controllable interior environmental condition, wherein the control signal effectuates control of the actuator to reduce the difference between the optimal biometric condition value and the sensed biometric condition value.

A detailed description of these and other non-limiting exemplary embodiments of a system and method for controlling an interior environmental condition in a vehicle is set forth below together with the accompanying drawings.

DETAILED DESCRIPTION

Figure 1:
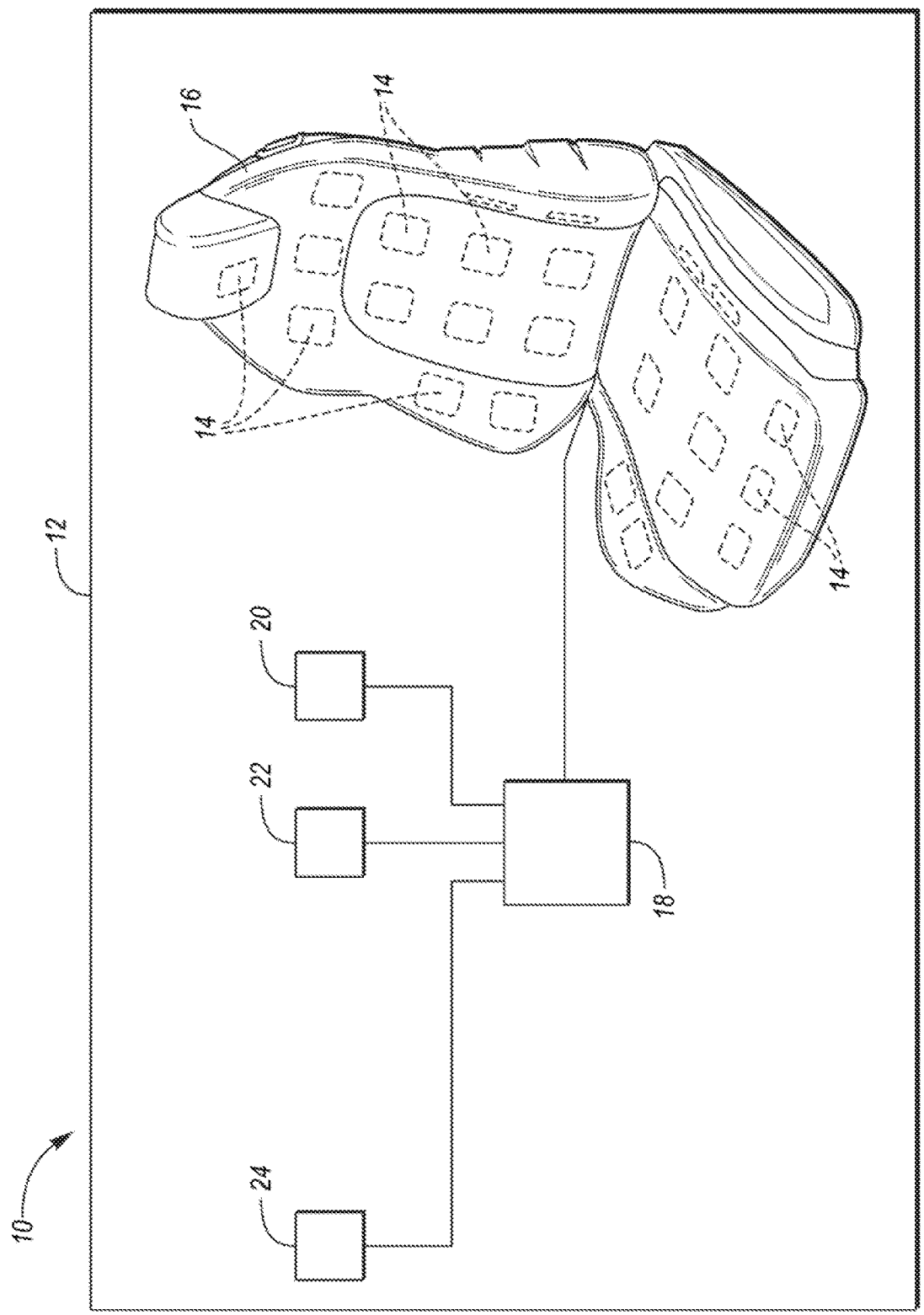
FIG. 1 is a block diagram illustrating a system for controlling an interior environmental condition in a vehicle according to one non-limiting exemplary embodiment of the present disclosure.

As required, detailed non-limiting embodiments are disclosed herein. However, it is to be understood that the disclosed embodiments are merely exemplary and may take various and alternative forms. The figures are not necessarily to scale, and features may be exaggerated or minimized to show details of particular components. Therefore, specific structural and functional details disclosed herein are not to be interpreted as limiting, but merely as a representative basis for teaching one skilled in the art.

With reference to FIGS. 1-6, a more detailed description of non-limiting exemplary embodiments of a system and method for controlling an interior environmental condition in a vehicle will be provided. For ease of illustration and to facilitate understanding, like reference numerals have been used herein for like components and features throughout the drawings.

As previously noted, automobile users often overcompensate conscious changes to vehicle system inputs as a means of correcting or adjusting their autonomic functions relating to physiological and/or phycological status. Moreover, interest in the automotive industry in intuitive human-machine interfaces (HMI), user systems, and memory-based occupant settings is high. In that regard, both vehicle OEMs and end user customers seek a dynamic, automatic, and seamless user experience, which can be a primary basis for quality perception.

The present disclosure describes a system and method by which, in general, a combination of occupant biometrics (autonomic/uncontrolled inputs, e.g., heart, lung, skin, brain, muscle function, etc.), interior vehicle conditions (user controlled, e.g., seat position, seat temperature, heating-ventilation-air-conditioning (HVAC), audio, etc.), as well as exterior vehicle conditions (environmental, e.g., time of day, day of the week, weather, likely destination of travel, etc.) are gathered long term, and a machine learning system may statistically analyze those inputs. The system and method continually assess based on such metrics how best to automatically adjust controllable interior conditions to place the occupant into the statistically optimal biometric levels given the exterior environment, e.g., driver in an alert but relaxed operation condition early in the morning.

In addition, the system and method of the present disclosure provide an intuitive HMI that automatically adjusts preferences based not just upon conscious subjective driver input patterns but also upon biometric autonomic reaction patterns. The present disclosure describes a system and method through which occupant specific autonomic activity in connection with the consciously controlled interior conditions as well as the uncontrolled exterior are monitored to bring the occupant into a desirable state via user specific data. The system and method of the present disclosure are thus unique in that they provide for the objective quantitative pairing of specific detailed biometric data (e.g., brain waves, heart activity, etc.) with environmental numerical data (e.g., temp, time, dates, angles, forces) to generate statistical dynamic profiles that evolve in vehicle and across platforms. The system and method of the present disclosure are distinct from existing systems in that they directly monitor the autonomic relationship intuitively over time to remove subjective errors that come with static profiles and which may continually improve with growing statistics and machine learning.

The system of the present disclosure may generally comprise an array of N various biometric and environmental sensors arranged within a seat structure to gather multiple condition inputs, where N may be any positive integer. Biometric sensors gather data, e.g., heart rate, breathing, brain activity, skin conductance, temperature, muscle tone, perspiration, etc., over an extended period of time to generate a dynamic user profile that assess user specific levels of biological and psychological condition in relation to non-biological conditions. Environmental sensors gather interior and exterior condition data, such as seat placement, seat temperature, audio level and preferences, HVAC settings, time of day, external weather, day of week, likely destination and travel time, etc., which are correlated to the biometric data.

These inputs may be stored, such as in a database, and may also be fed into a machine learning system, which may be of any known type. Such inputs may be used to generate a user profile, which may be dynamic and increasingly accurate over time based not just on conscious user inputs but optimal user specific biometrics. Such a user profile may be used to automatically adjust controllable conditions, e.g., seat positions, temperature (seat and HVAC), audio level and output sounds, etc. This information can follow the user via mobile device (e.g., smart phone) or cloud-based storage and communication to offer universal dynamic profile settings and reactions in multiple vehicles, Which may thereby expand upon the learning capabilities.

Referring now to FIG. 1, a block diagram illustrating a system for controlling an interior environmental condition in a vehicle according to one non-limiting exemplary embodiment of the present disclosure is shown. As seen therein, a system 10 is provided for controlling an interior environmental condition in a vehicle 12. In that regard, the system 10 may perform the operations, functions, and/or method described herein. The system may comprise an array of N biometric sensors 14 for sensing occupant biometric conditions, where N is a positive integer. Each biometric sensor 14 may be adapted to be mounted in a vehicle seat 16 and configured to sense a biometric condition of an occupant (not shown) of the seat 16 and generate a signal representative of a value of the sensed biometric condition.

The system 10 may further comprise a controller 18 that may be adapted to be mounted in the vehicle and may be configured to receive the biometric condition signal. The controller 18 may also be configured to receive an interior environmental condition signal representative of a value of a sensed controllable interior environmental condition, and an exterior environmental condition signal representative of a value of a sensed exterior environmental condition. Each of a plurality of exterior environmental condition values may have associated therewith a biometric condition value defined as an optimal biometric condition value for the vehicle occupant for the corresponding exterior environmental condition value.

The controller 18 may be further configured to determine the optimal biometric condition value for the vehicle occupant associated with the sensed exterior environmental condition value, as well as compare the optimal biometric condition value for the vehicle occupant to the sensed biometric condition value. The controller 18 may be still further configured to, in response to a difference between the optimal biometric condition value and the sensed biometric condition value, generate a control signal to control an actuator 20 configured to control the controllable interior environmental condition, wherein the control signal effectuates control of the actuator 20 to reduce the difference between the sensed biometric condition value and the optimal biometric condition value.

Still referring to FIG. 1, the system 10 may optionally further comprise one or more vehicle interior sensors 22 adapted to be mounted in the vehicle and configured to sense the controllable interior environmental condition in the vehicle 12 and generate the signal representative of the value of the sensed interior environmental condition. The system 10 may also optionally further comprise one or more vehicle exterior sensors 24 adapted to be mounted in the vehicle 12 and configured to sense the environmental condition exterior to the vehicle 12 and generate the signal representative of the value of the sensed exterior environmental condition.

The biometric condition or conditions of the vehicle occupant sensed by the biometric sensors 14 may comprise one or more of cardiac activity, blood pressure (e.g., venous and/or arterial), blood rheology, blood oxygenation, blood saturation, respiratory activity, temperature, perspiration, conductance, musculoskeletal activity, and/or brain waves of the occupant. Additionally, image and/or infrared (IR) based biometric sensors (not shown) may be adapted to be mounted anywhere in the vehicle and may be configured to sense the occupant gaze level, occupant gaze direction, pupillometry, occupant head position, level of occupant eyelid closure, and/or an occupant facial or extremities thermal map. Such image and/or IR sensed occupant biometric conditions may be used or employed in the system 10 and method of the present disclosure as described herein in conjunction with those occupant biometric conditions sensed by biometric sensors 14 adapted to be mounted in a vehicle seat and configured to sense those biometric conditions previously described.

The controllable interior environmental condition or conditions of the vehicle 12 may comprise one or more of a seat position, seat temperature, vehicle interior or cabin temperature, audio level, ventilation setting, healing setting, cooling setting, and/or lighting condition. In that regard, the actuator 20 configured to control the controllable interior environmental condition to reduce the difference between the sensed biometric condition value and the optimal biometric condition value may comprise one or more actuators 20 configured to control an interior environmental condition or conditions such as a seat position, seat temperature, vehicle interior or cabin temperature, audio level, ventilation setting, heating setting, cooling setting, and/or lighting condition. The exterior environmental condition or conditions outside the vehicle 12 may comprise one or more of a time of day, day of week, date, season, weather condition, light condition, travel destination, travel time, traffic density, road type, and/or topography. Other biometric conditions, vehicle interior environmental conditions, and/or vehicle exterior environmental condition(s) may also or alternatively be sensed or controlled.

While shown in FIG. 1 as separate from the vehicle seat 16, the vehicle interior sensor or sensors 22 may be adapted to be mounted in the vehicle seat 16. The vehicle interior sensor or sensors 22 may as well or alternatively be adapted to be mounted at any location in the vehicle 12. Similarly, while also shown in FIG. 1 as separate from the vehicle seat 16, the controller 18 may be adapted to be mounted in the vehicle seat 16. The controller 18 may alternatively be adapted to be mounted at any location in the vehicle 12. Alternatively, the controller 18 may be located remotely from the vehicle 12, such as in the form or part of server in a cloud-based environment.

As one skilled in the art would understand, the controller 18 and any other unit, system, subsystem, sensor, module, device, or the like described herein may individually, collectively, or in any combination comprise appropriate circuitry, such as one or more appropriately programmed processors (e.g., one or more microprocessors including central processing units (CPU)) and associated memory, which may include stored operating system software and/or application software executable by the processor(s) for controlling operation thereof and for performing the particular algorithm or algorithms represented by the various functions and/or operations described herein, including interaction between and/or cooperation with each other. One or more of such processors, as well as other circuitry and/or hardware, may be included in a single ASIC (Application-Specific Integrated Circuitry), or several processors and various circuitry and/or hardware may be distributed among several separate components, whether individually packaged or assembled into a SoC (System-on-a-Chip). As well, the controller 18 may be located remotely from the vehicle 12, such as in the form or part of server in a cloud-based environment. The controller 18 may therefore comprise a processor and an associated storage medium having stored computer executable instructions for performing the particular algorithm or algorithms represented by the various functions and/or operations described herein, which may include any type of known learning algorithm.

With continuing reference to FIG. 1, the vehicle seat 16 may be a driver seat and the occupant may be a driver of the vehicle 12. Alternatively, the vehicle seat 16 may be a non-driving passenger seat and the occupant may be a non-driving passenger of the vehicle 12. In that regard, an occupant may have associated therewith a first occupant profile as a driver and a second occupant profile as a non-driving passenger. Each of the first and second occupant profiles may comprise a biometric condition value, interior environmental condition value, and external environmental condition value, and the first occupant profile may be different from the second occupant profile.

In that regard, the controller 18 may be configured to store in an associated memory or a vehicle storage medium an occupant profile comprising a biometric condition value, interior environmental condition value, and external environmental condition value, and/or other information The controller 18 may as well or alternatively be configured to communicate with a personal device of the occupant to download and store such an occupant profile. The controller 18 may as well or alternatively be configured to communicate with a server external to the vehicle (e.g., cloud-based storage) to download and store such an occupant profile. In that same regard, the controller 18 may also be configured to dynamically modify the occupant profile based on sensed biometric condition values, sensed interior environmental condition values, and sensed external environmental condition values, and to store a modified occupant profile in the associated memory or vehicle storage medium, upload a modified occupant profile to the server, and/or to upload a modified occupant profile to the personal device. The controller 18 may therefore include and/or be configured for operation with communication circuitry (not shown), which may include a communication unit or interface and one or more antennas, appropriate for such purposes and such communication may comprise any known type of wired or wireless communication, including cellular, dedicated short range communication (DSRC), wireless local area network (WLAN), near field communication (NFC), Bluetooth, or any other type known, for communication with the units, devices, storage, or the like in the manner and for the purposes described herein.

Figure 2:
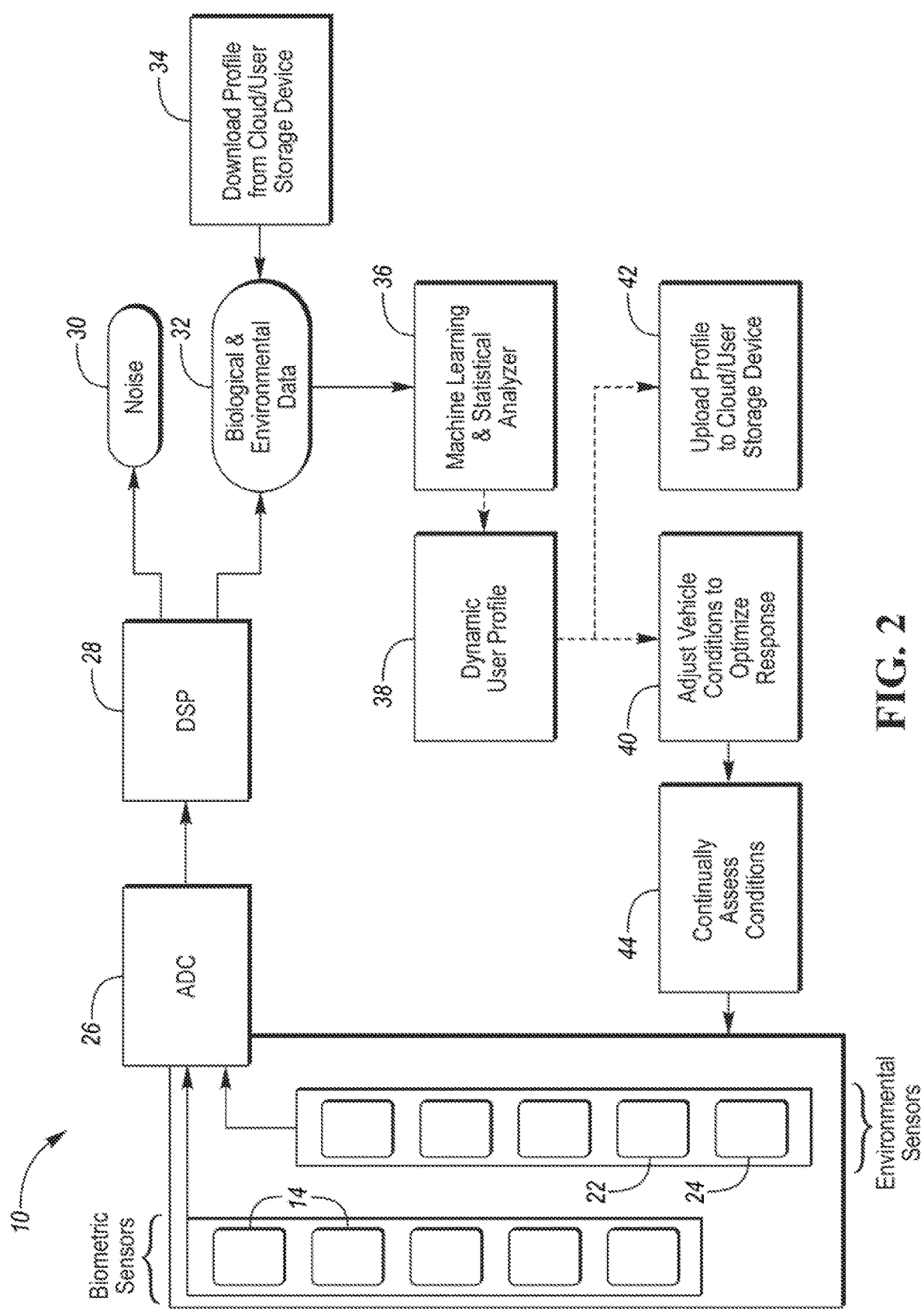
FIG. 2 is an overall functional block diagram of a system for controlling an interior environmental condition in a vehicle according to one non-limiting exemplary embodiment of the present disclosure.

Referring next to FIG. 2, an overall functional block diagram of a system 10 and method for controlling an interior environmental condition in a vehicle according to one non-limiting exemplary embodiment of the present disclosure is shown. As seen therein, a plurality of biometric sensors 14 may sense vehicle occupant biometric conditions, and a plurality of vehicle interior environmental condition sensors 22 and vehicle exterior environmental sensors 24 may sense vehicle interior and exterior environmental conditions.

Signals representative of values of the sensed biometric conditions and vehicle interior and exterior environmental conditions may be provided by the sensors 14, 22, 24 to an analog-to-digital converter (ADC) 26 and then to a digital signal processor (DSP) 28. The DSP 28 may be configured to filter out noise 30 from such signals to provide biological and environmental data 32. The biological and environmental data 32 may be combined, complemented, supplemented, and/or augmented with user profile data or information as previously described, which may be retrieved and/or downloaded 34 from memory, vehicle storage, cloud-based storage, and/or user mobile device storage.

The biological and environmental data 32 may be fed to a machine learning and statistical analyzer 36, which may be of any known type, which may be configured to produce a dynamic user profile 38. The biological and environmental data 32 and user profile 38 may be used to adjust 40 vehicle interior conditions to optimize occupant biometric response. The dynamic user profile may also be uploaded and/or stored 42 to memory, vehicle storage, cloud-based storage, and/or user mobile device storage. After adjustment 40 of vehicle interior conditions, occupant biometric conditions and vehicle interior environmental conditions may be continually assessed 44 by sensors 14, 22 and may be provided again to ADC 26 and DSP 28 for further processing and potentially further adjustment 40 of vehicle interior environmental conditions and/or user profile 38.

Figure 3A:
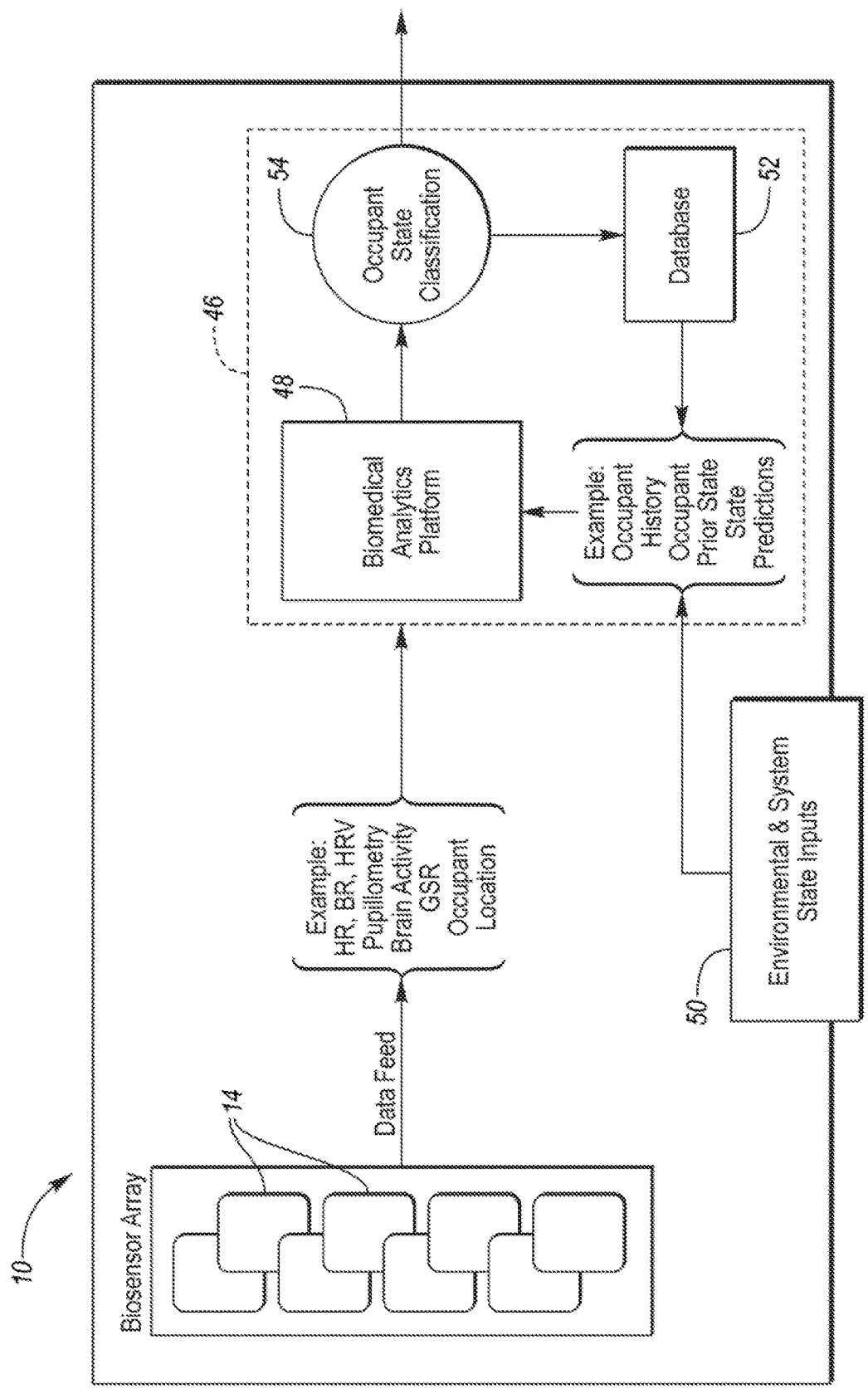
FIG. 3A is a simplified functional block diagram of a first portion of a system for controlling an interior environmental condition in a vehicle according to one non-limiting exemplary embodiment of the present disclosure.

Referring now to FIG. 3A, a simplified functional block diagram of a first portion of a system 10 and method for controlling an interior environmental condition in a vehicle according to one non-limiting exemplary embodiment of the present disclosure is shown. As seen therein, the first portion of the system 10 and method is directed to occupant monitoring and may include a reinforced learning feedback loop 46. An array of biometric sensors 14 may sense occupant biometric conditions, which may for example include heart rate, breathing rate, heart rate variability, pupillometry, brain activity, galvanic skin resistance (GSR), and/or occupant location, which data may be provided to a biomedical analytics platform 48 in the reinforced learning feedback loop 46.

Vehicle interior/exterior environmental and vehicle system state inputs 50, which may for example include associated occupant biometric history data, occupant prior state biometric data, and/or vehicle system state predictions, may also be provided to the biomedical analytics platform 48 in the reinforced learning feedback loop 46. Such vehicle environmental and system state inputs 50 may also or alternatively be provided to the biomedical analytics platform 48 in the reinforced learning feedback loop 46 from a database 52 for storing such inputs 50 and other information.

In the reinforced learning feedback loop 46, the biomedical analytics platform 48 may determine an occupant state classification 54 based on the occupant biometric condition data received from the biometric sensors 14 and the received vehicle environmental and system state inputs 50. The occupant state classification 54 determination may be stored in the database 52 and fed back to the biomedical analytics platform 48 for iterative or recursive determination thereof based also on occupant biometric condition data repeatedly or continuously provided by biometric sensors 14.

Figure 3B:
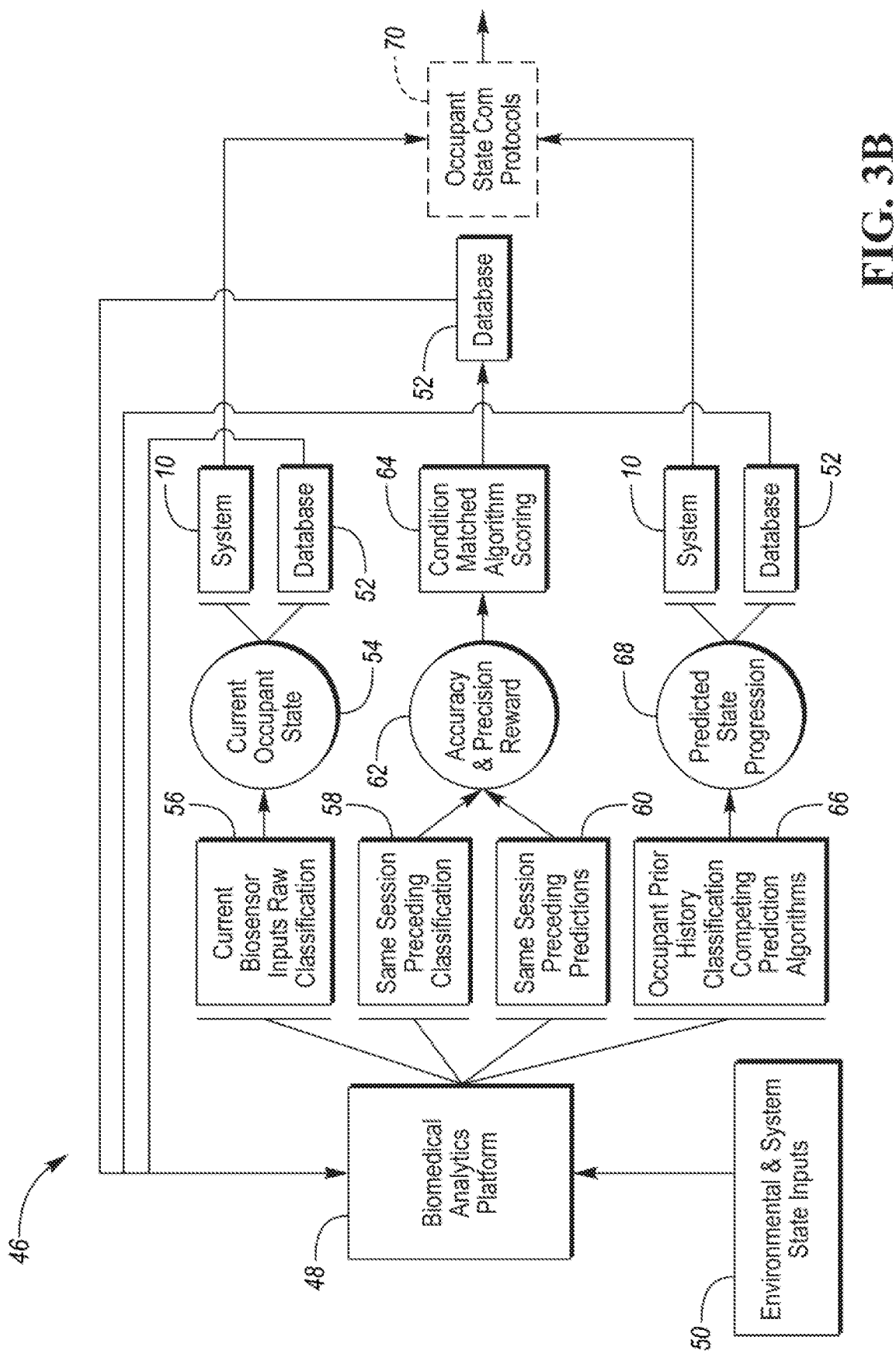
FIG. 3B is a detailed functional block diagram of a first portion of a system for controlling an interior environmental condition in a vehicle according to one non-limiting exemplary embodiment of the present disclosure.

Referring next to FIG. 3B, a detailed functional block diagram of a first portion of a system 10 and method for controlling an interior environmental condition in a vehicle according to one non-limiting exemplary embodiment of the present disclosure is shown. In that regard, a reinforced learning feedback loop 46 such as that described above in connection with FIG. 3A is illustrated in greater detail. As seen in FIG. 3B and as previously described, vehicle environmental and system state inputs 50 may be provided to the biomedical analytics platform 48.

The biomedical analytics platform 48 may utilize current biometric sensor inputs and a raw occupant classification 56 to determine a current occupant state 54, which may be provided to both the system 10 and the database 52. The biomedical analytics platform 48 may also utilize a preceding occupant classification 58 and preceding predictions 60 from a same (i.e., current) system session to determine the accuracy and precision 62 of such preceding classification 58 and preceding predictions 60. The determined accuracy and precision. 62 of such preceding classifications 58 and preceding prediction 60 may be subjected to condition matched algorithm scoring 64 of any known type and stored in the database 52. The biomedical analytics platform 48 may further utilize an occupant prior history classification 66 from competing prediction algorithms, which may be of any known type, to determine a predicted state progression 68, which may be provided to both the system 10 and the database 52.

The current occupant state 54 determination, the accuracy and precision 62 determination, and the predicted state progression 68 determination stored in the database 52 may be fed back to the biomedical analytics platform 48 for iterative or recursive determination thereof based also on vehicle environmental and state system inputs 50 repeatedly or continuously provided to the biomedical analytics platform 48. As well, the system 10 and method determine occupant state component protocols 70 based on the current occupant sate 54 determination and the predicted occupant state progression 68 determination.

Figure 4A:
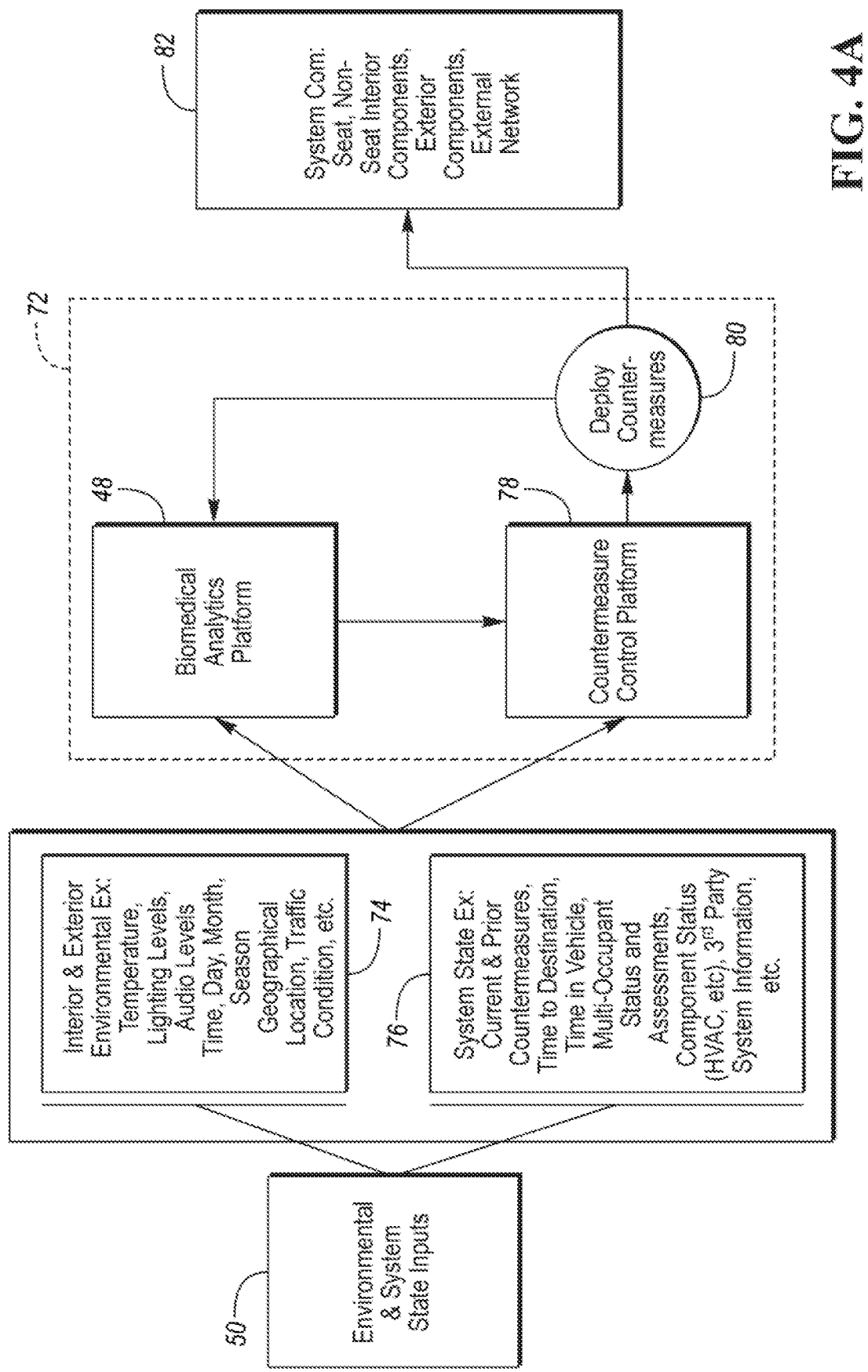
FIG. 4A is a simplified functional block diagram of a second portion of a system for controlling an interior environmental condition in a vehicle according to one non-limiting exemplary embodiment of the present disclosure.

Referring now to FIG. 4A, a simplified functional block diagram of a second portion of a system 10 and method for controlling an interior environmental condition in a vehicle according to one non-limiting exemplary embodiment of the present disclosure is shown. As seen therein, the second portion of the system 10 and method is directed to vehicle interior and exterior environment monitoring and may include a reinforced learning feedback loop 72.

The vehicle environmental and system state inputs 50 may include vehicle interior and exterior environmental conditions 74 and vehicle system state information 76. In that regard, as previously described, vehicle interior and exterior environmental conditions 74 may comprise one or more of interior temperature, exterior temperature, interior lighting level, exterior lighting level, audio level, time of day, day of week, month, date, season, weather condition, geographic location, traffic conditions (e.g., traffic density), road type, topography, and/or others. Vehicle system state information 76 may comprise one or more of current and/or prior countermeasures employed in response to sensed occupant biometric conditions, time to destination, time in vehicle, multi-occupant status, occupant assessments, vehicle component status (e.g., seat position, seat temperature, HV C settings, audio settings, etc.), third-party system information, and/or others.

Such vehicle environmental and system state inputs 50 may be provided to the biomedical analytics platform 48 in the reinforced learning feedback loop 72, as well as to a countermeasures control platform 78. The biomedical analytics platform 48 may provide occupant state 54 and/or predicted occupant state progression 68 information to the countermeasure control platform 78, based on which the countermeasure control platform 78 determines and deploys countermeasures 80 to control, adjust, affect, change, and/or optimize sensed occupant biometric conditions. Such countermeasures 80 may comprise adjusting and/or controlling vehicle system component settings 82 such as a vehicle seat (e.g., position, temperature), vehicle interior components (e.g., HVAC settings, interior lighting settings), vehicle exterior components (e.g., headlights), and/or external network settings.

Figure 4B:
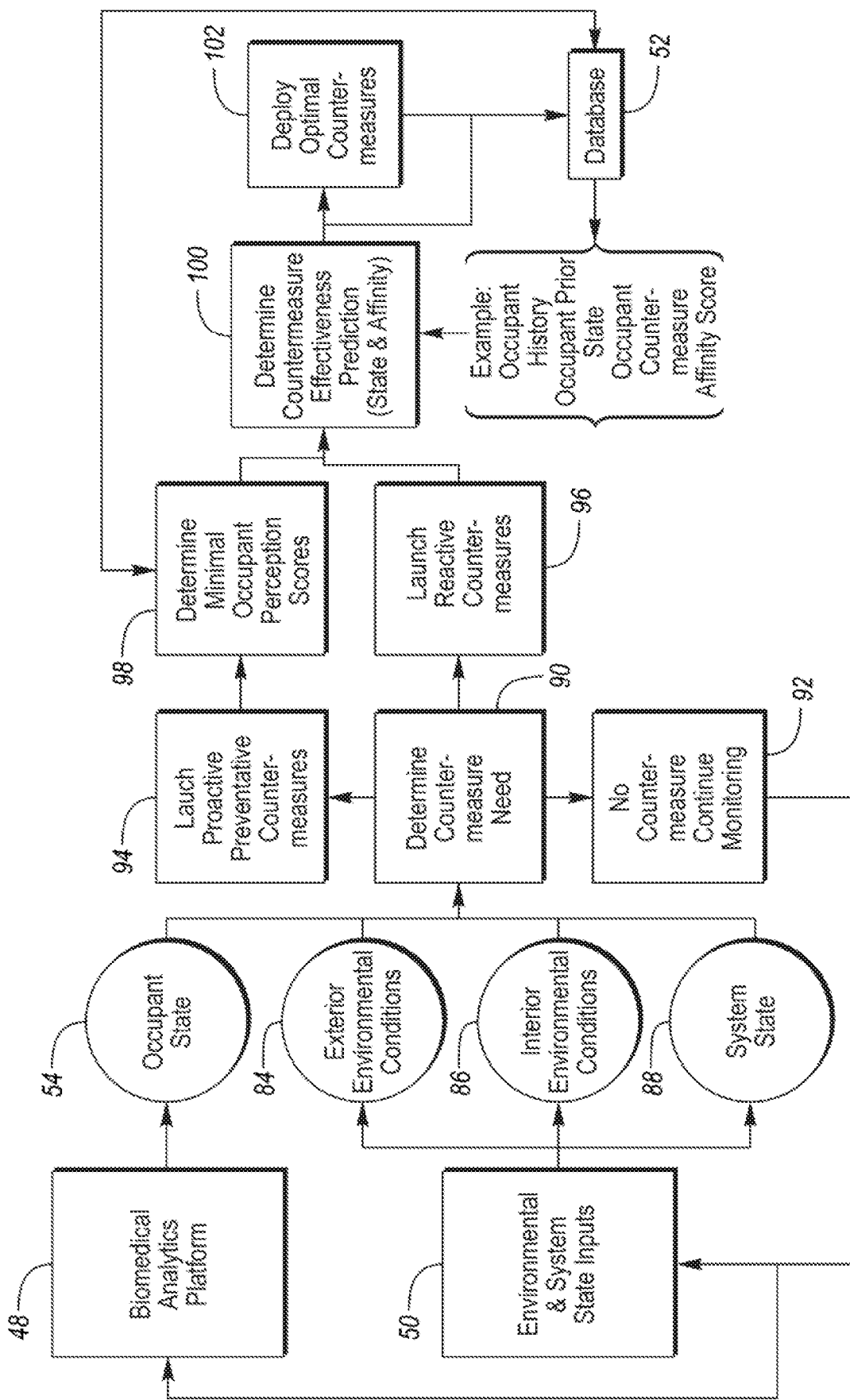
FIG. 4B is a detailed functional block diagram of a second portion of a system for controlling an interior environmental condition in a vehicle according to one non-limiting exemplary embodiment of the present disclosure.

Referring next to FIG. 4B, a detailed functional block diagram of a second portion of a system 10 and method for controlling an interior environmental condition in a vehicle according to one non-limiting exemplary embodiment of the present disclosure is shown. In that regard, a reinforced learning feedback loop 72 such as that described above in connection with FIG. 4A is illustrated in greater detail. As seen in FIG. 4B and as previously described, biomedical analytics platform 48 may determine a vehicle occupant state 54, and vehicle environmental and system slate inputs 50 may provide vehicle exterior environmental conditions 84, vehicle interior environmental conditions 86, and vehicle system state information 88.

Based on the vehicle occupant state 54, vehicle exterior environmental conditions 84, vehicle interior environmental conditions 86, and vehicle system state information 88, the system 10 and method may determine 90 whether one or more countermeasures are needed. When the system 10 and method determine that no countermeasures are needed, monitoring and/or analysis of occupant biometric conditions and vehicle interior/exterior environmental condition may continue 92. Alternatively, when the system 10 and method determine that countermeasures are needed, proactive 94 and/or reactive 96 countermeasures may be launched or identified. In that regard, proactive countermeasures 94 may be employed to maintain current occupant biometric conditions or address predicted occupant biometric conditions, while reactive countermeasures 96 may be employed to modify changing occupant biometric conditions. For proactive countermeasures 94, the system 10 and method may also determine minimal occupant perception scores 98.

For each proactive 94 and/or reactive 96 countermeasure identified, the system 10 and method may also determine or calculate an effectiveness prediction 100, including state and affinity. In that regard, such a prediction 100 may be based on or utilize data relating to or associate with occupant biometric history, occupant prior state information, and/or an occupant countermeasure affinity score, which data may be stored in and provided by database 52. Based on the effectiveness prediction 100, the system 10 and method may determine and deploy 102 one or more optimal countermeasures, which may be proactive 94 and/or reactive 96, which determination and action may also be stored in the database 52.

Figure 5A:
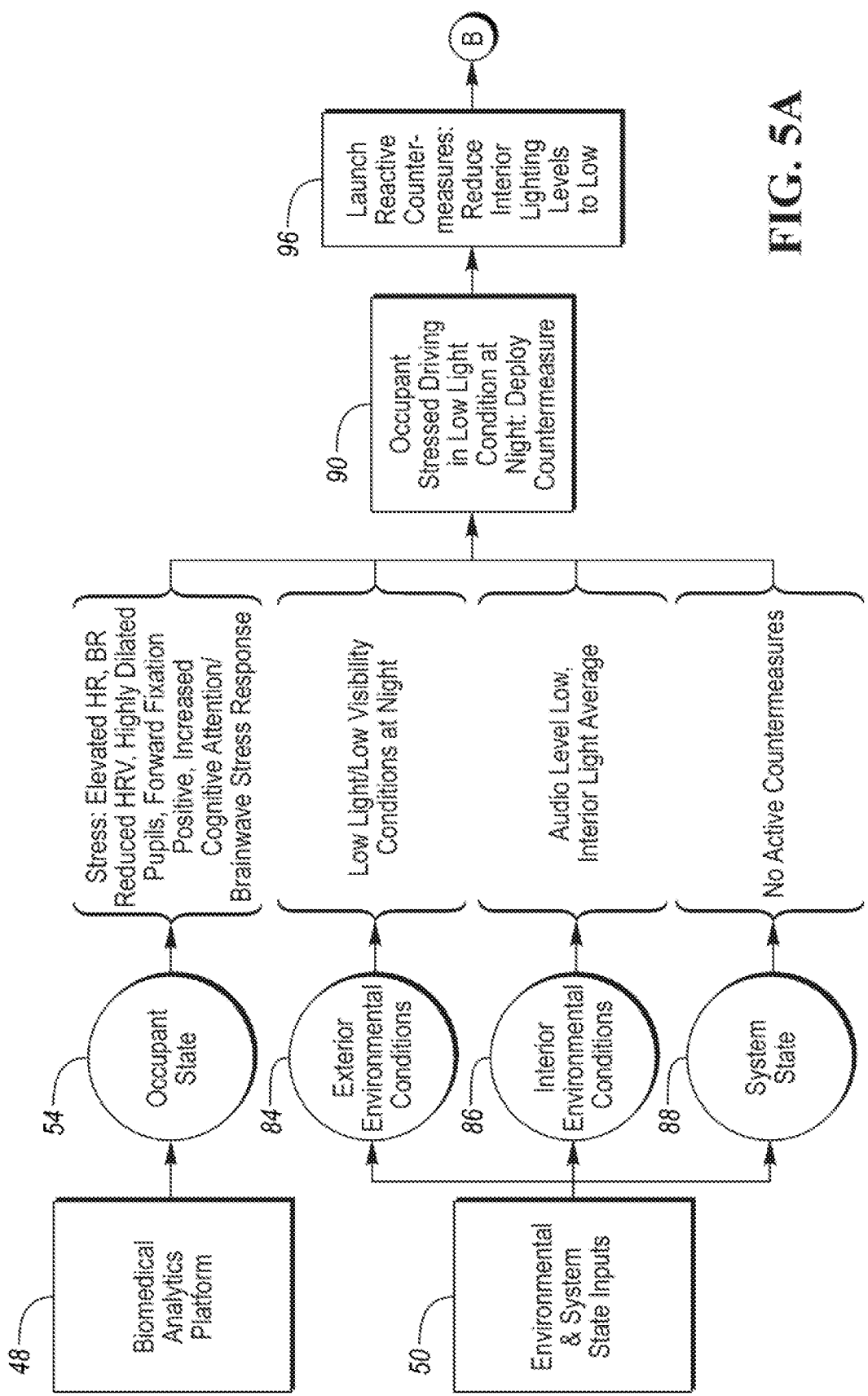
FIG. 5A is a functional block diagram illustrating an example situation in a system for controlling an interior environmental condition in a vehicle according to one non-limiting exemplary embodiment of the present disclosure.
Figure 5B:
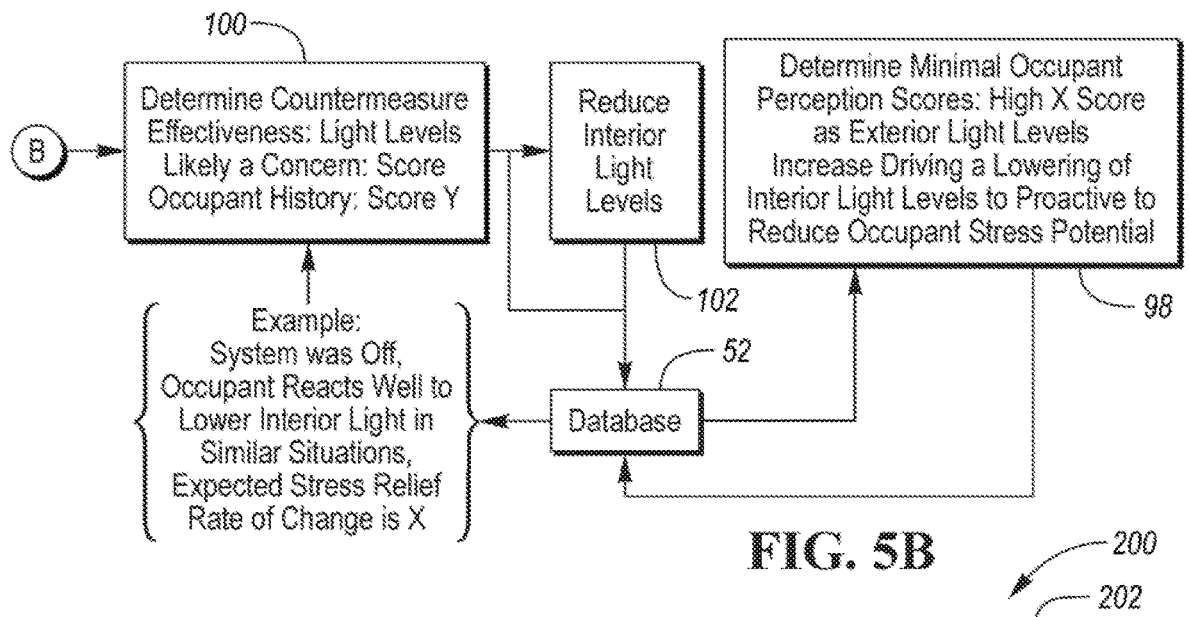
FIG. 5B is a functional block diagram illustrating an example situation in a system for controlling an interior environmental condition in a vehicle according to one non-limiting exemplary embodiment of the present disclosure.

Referring now to FIGS. 5A and 5B, a functional block diagram illustrating an example situation in a system 10 and method for controlling an interior environmental condition in a vehicle according to one non-limiting exemplary embodiment of the present disclosure is shown. As seen in FIG. 5A, biomedical analytics platform 48 may determine a vehicle occupant state 54, which for example may be a state of stress which may be defined or determined by the occupant's heart and/or breathing rates elevated above threshold values, the occupant's pupils dilated beyond a threshold level, a positive determination that the occupant has a forward fixation based on head position or gaze direction, a determination that the occupant has an cognitive attention level above a threshold value based on brainwave activity, and for a brainwave response indicative of stress.

Moreover, vehicle environmental and system state inputs 50 may provide vehicle exterior environmental conditions 84, vehicle interior environmental conditions 86, and vehicle system state information 88. As seen in FIG. 5A, vehicle exterior environmental conditions 84 may for example include low light and/or visibility levels below threshold values due to nighttime conditions. The vehicle interior environmental conditions 86 may for example include a low audio level below a threshold value and/or an average lighting level between upper and lower threshold values. The vehicle system state information 88 may for example indicate that no countermeasures are currently active.

Based on these vehicle occupant state 54, vehicle exterior environmental conditions 84, vehicle interior environmental conditions 86, and vehicle system state information 88, the system 10 and method may determine that the vehicle occupant (e.g., driver) is experiencing stress due to driving in low light conditions at night and that, as a result, countermeasures are needed 90. In this example, the system 10 and method may launch or identify reactive countermeasures 96 to reduce vehicle interior light levels to low, i.e., below a threshold value.

With reference to FIG. 5B, for the reactive countermeasure 96 identified to lower vehicle interior light levels, the system 10 and method may also determine or calculate an effectiveness prediction 100, which may be based on whether the vehicle interior light level is likely to be a concern to the occupant as well as occupant biometric history. More specifically, in this example, the effectiveness prediction 100 may be based on information or data indicating that the system 10 was off, the occupant has reacted well to light levels below the threshold value in similar situations, and/or an expected or predicted stress relief rate of change that exceeds a threshold value, which data may be stored in and provided by database 52. In this example, based on the effectiveness prediction 100, the system 10 and method may determine as optimal and deploy 102 the countermeasure of reducing vehicle interior light levels, which determination and action may also be stored in the database 52. Moreover, for potential future use as a proactive countermeasure, the system 10 and method may also determine 98 minimal occupant perception scores, where a high occupant perception score above a threshold value as vehicle exterior light levels increase drives or results in a lowering of vehicle interior light levels as exterior light levels decrease to thereby proactively reduce, prevent, and/or mitigate occupant stress potential.

Figure 6:
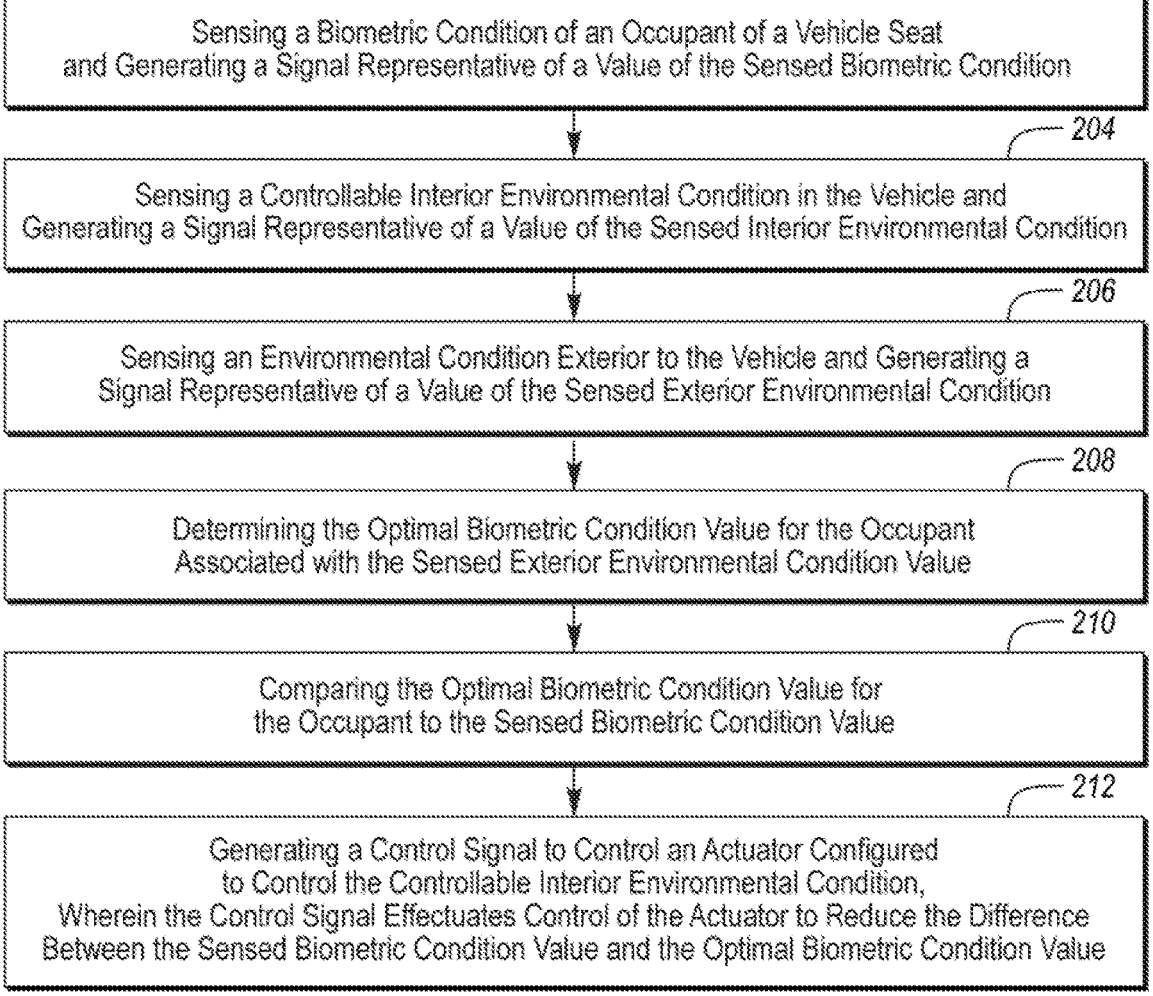
FIG. 6 is a flow chart illustrating a method for controlling an interior environmental condition in a vehicle according to one non-limiting exemplary embodiment of the present disclosure.

Referring next to FIG. 6, a flow chart illustrating a method 200 for controlling an interior environmental condition in a vehicle according to one non-limiting exemplary embodiment of the present disclosure is shown. It should be noted that the method 200 may be performed by the system 10 as described in detail above. As seen in FIG. 6, the method 200 may comprise sensing 202 a biometric condition of an occupant of a vehicle seat and generating a signal representative of a value of the sensed biometric condition, sensing 204 a controllable interior environmental condition in the vehicle and generating a signal representative of a value of the sensed interior environmental condition, and sensing 206 an environmental condition exterior to the vehicle and generating a signal representative of a value of the sensed exterior environmental condition.

As previously described, each of a plurality of exterior environmental condition values may have associated therewith a biometric condition value defined as an optimal biometric condition value for the occupant for the corresponding exterior environmental condition value. The method 200 may further comprise determining 208 the optimal biometric condition value for the occupant associated with the sensed exterior environmental condition value, and comparing 210 the optimal biometric condition value for the occupant to the sensed biometric condition value. The method may further comprise, in response to a difference between the optimal biometric condition value and the sensed biometric condition value, generating 212 a control signal to control an actuator configured to control the controllable interior environmental condition, wherein the control signal effectuates control of the actuator to reduce the difference between the sensed biometric condition value and the optimal biometric condition value.

As also described previously, the biometric condition or conditions sensed may comprise one or more of cardiac activity, blood pressure, blood rheology, blood oxygenation, blood saturation, respiratory activity, temperature, perspiration, conductance, musculoskeletal activity, and/or brain wave activity. The controllable interior environmental condition or conditions may comprise one or more of a seat position, seat temperature, interior temperature, audio level, ventilation setting, heating setting, cooling setting, and/or lighting condition. The exterior environmental condition or conditions may comprise one or more of a time of day, day of week, date, season, weather condition, light condition, travel destination, travel time, traffic density, road type, and/or topography. Other biometric conditions, vehicle interior environmental conditions, and/or vehicle exterior environmental condition(s) may also or alternatively be sensed or controlled.

The system 10 and/or method 200 may be implemented and/or performed at least partially by or in conjunction with a non-transitory computer readable storage medium having stored computer executable instructions. In that regard, such computer executable instructions may be for controlling an interior environmental condition in a vehicle comprising a biometric sensor configured to sense a biometric condition of an occupant of a vehicle seat and generate a signal representative of a value of the sensed biometric condition, a vehicle interior sensor configured to sense a controllable interior environmental condition in the vehicle and generate a signal representative of a value of the sensed interior environmental condition, a vehicle exterior sensor configured to sense an environmental condition exterior to the vehicle and generate a signal representative of a value of the sensed exterior environmental condition, wherein a controller is configured to receive the biometric condition signal, the interior environmental condition signal, and the exterior environmental condition signal. As previously described, each of a plurality of exterior environmental condition values may have associated therewith a biometric condition value defined as an optimal biometric condition value for the occupant for the corresponding exterior environmental condition value.

The computer executable instructions may be configured to cause the controller to determine the optimal biometric condition value for the occupant associated with the sensed exterior environmental condition value, and compare the optimal biometric condition value for the occupant to the sensed biometric condition value. The computer executable instructions may be further configured to cause the controller to, in response to a difference between the optimal biometric condition value and the sensed biometric condition value, generate a control signal to control an actuator configured to control the controllable interior environmental condition, wherein the control signal effectuates control of the actuator to reduce the difference between the sensed biometric condition value and the optimal biometric condition value.

The biometric condition or conditions sensed may again comprise one or more of cardiac activity, blood pressure, blood rheology, blood oxygenation, blood saturation, respiratory activity, temperature, perspiration, conductance, musculoskeletal activity, and/or brain wave activity. The controllable interior environmental condition or conditions may comprise one or more of a seat position, seat temperature, interior temperature, audio level, ventilation setting, heating setting, cooling setting, and/or lighting condition. The exterior environmental condition or conditions may comprise one or more of a time of day, day of week, date, season, weather condition, light condition, travel destination, travel time, traffic density, road type, and/or topography. Other biometric conditions, such as those previously described herein, vehicle interior environmental conditions, and/or vehicle exterior environmental condition(s) may also or alternatively be sensed or controlled.

Thus, the present disclosure provides a system and method capable of automatically monitoring user autonomic functions and setting and/or adjusting vehicle conditions accordingly. The system and method provide for integration of neuro-monitoring (e.g, electro-encephalogram (EEG)) with other user biometrics and may utilize a long-term machine learning algorithm to provide for objective assessments that may be combined with subjective trends and both internal and external vehicle conditions. The system and method automatically adjust vehicle conditions to put an occupant in the best scenarios based not on generalized ease study data but also upon the occupant's own biometric inputs, surrounding conditions, and a continuously learning machine, thereby creating a highly personalized user experience in vehicle.

The system and method of the present disclosure is capable of monitoring, learning, and reacting in such a fashion to mitigate the problem of user over reaction or overcompensation described above. The system and method also enable creation of a customized user profile, which may be dynamic. The user profile may also be shared so that other vehicle systems beyond the user's own vehicle systems would be able not only adjust to the user but also continue to learn and customize to the user.

The system and method of the present disclosure thereby improves vehicle conditions to positively benefit occupant autonomic function (e.g., stress, drowsiness, etc.) and provide considerable short-term and long-term health and safety benefits. Moreover, the system and method of the present disclosure are able not only to transmit but also receive data from multiple seat locations and vehicles to share and update information, thereby improving user quality perception and user experience. The system design and method of the present disclosure thus may be particularly useful in fully autonomous vehicles.

As is readily apparent from the foregoing, various non-limiting embodiments of a system and method for controlling an interior environmental condition in a vehicle have been described. While various embodiments have been illustrated and described herein, they are exemplary only and it is not intended that these embodiments illustrate and describe all those possible. Instead, the words used herein are words of description rather than limitation, and it is understood that various changes may be made to these embodiments without departing from the spirit and scope of the following claims.

What is claimed is:

1. A system for controlling an interior environmental condition in a vehicle, the system comprising:
   a biometric sensor to sense a biometric condition of an occupant of a vehicle seat and generate a signal representative of a value of the sensed biometric condition; and
   a controller to receive the biometric condition signal, an interior environmental condition signal representative of a value of a sensed controllable interior environmental condition, and an exterior environmental condition signal representative of a value of a sensed exterior environmental condition;
   wherein each of a plurality of exterior environmental condition values has associated therewith a biometric condition value defined as an optimal biometric condition value for the occupant for the corresponding exterior environmental condition value;
   wherein the controller is configured to
      determine the optimal biometric condition value for the occupant associated with the sensed exterior environmental condition value,
      compare the optimal biometric condition value for the occupant to the sensed biometric condition value, and
      in response to a difference between the optimal biometric condition value and the sensed biometric condition value, generate a control signal to control an actuator to control the controllable interior environmental condition, wherein the control signal effectuates control of the actuator to reduce the difference between the sensed biometric condition value and the optimal biometric condition value; and
   wherein the controller is further to
      receive an occupant profile comprising a biometric condition value, interior environmental condition value, and external environmental condition value, and
      dynamically modify the occupant profile based on sensed biometric condition values, sensed interior environmental condition values, and sensed external environmental condition values, and generate a modified occupant profile comprising a biometric condition value, interior environmental condition value, and external environmental condition value.

2. The system of claim 1 further comprising:
   a vehicle interior sensor to sense the controllable interior environmental condition in the vehicle and generate the signal representative of the value of the sensed interior environmental condition; and
   a vehicle exterior sensor to sense the environmental condition exterior to the vehicle and generate the signal representative of the value of the sensed exterior environmental condition.

3. The system of claim 2 wherein the vehicle interior sensor is mountable in the vehicle seat.

4. The system of claim 1 wherein the biometric condition comprises at least one of cardiac activity, blood pressure, blood rheology, blood oxygenation, blood saturation, respiratory activity, temperature, perspiration, conductance, musculoskeletal activity, and brain waves.

5. The system of claim 1 wherein the controllable interior environmental condition comprises at least one of a seat position, seat temperature, interior temperature, audio level, ventilation, heating setting, cooling setting, and lighting condition.

6. The system of claim 1 wherein the exterior environmental condition comprises at least one of a time of day, day of week, date, season, weather condition, light condition, travel destination, travel time, traffic density, road type, and topography.

7. The system of claim 1 wherein the vehicle seat is a driver seat and the occupant is a driver of the vehicle.

8. The system of claim 1 wherein the vehicle seat is a non-driving passenger seat and the occupant is a non-driving passenger of the vehicle.

9. The system of claim 1 wherein the occupant has associated therewith a first occupant profile as a driver and a second occupant profile as a non-driving passenger, each of the first and second occupant profiles comprising a biometric condition value, interior environmental condition value, and external environmental condition value, and wherein the first occupant profile is different from the second occupant profile.

10. The system of claim 1 wherein the controller is mountable in the vehicle seat.

11. The system of claim 1 wherein the controller comprises a processor and an associated non-transitory storage medium having stored computer executable instructions comprising a learning algorithm.

12. The system of claim 1 wherein the controller is to communicate with a server external to the vehicle to download and store the occupant profile comprising a biometric condition value, interior environmental condition value, and external environmental condition value.

13. The system of claim 12 wherein the controller is to upload the modified occupant profile to the server.

14. The system of claim 1 wherein the controller is to communicate with a personal device of the occupant to download and store the occupant profile comprising a biometric condition value, interior environmental condition value, and external environmental condition value.

15. The system of claim 14 wherein the controller is to upload the modified occupant profile to the personal device.

16. The system of claim 1 wherein the controller is to store in a vehicle storage medium the occupant profile comprising a biometric condition value, interior environmental condition value, and external environmental condition value.

17. The system of claim 16 wherein the controller is to store the modified occupant profile in the vehicle storage medium.

18. A method for controlling an interior environmental condition in a vehicle, the method comprising:
sensing a biometric condition of an occupant of a vehicle seat and generating a signal representative of a value of the sensed biometric condition;
sensing a controllable interior environmental condition in the vehicle and generating a signal representative of a value of the sensed interior environmental condition;
sensing an environmental condition exterior to the vehicle and generating a signal representative of a value of the sensed exterior environmental condition;
wherein each of a plurality of exterior environmental condition values has associated therewith a biometric condition value defined as an optimal biometric condition value for the occupant for the corresponding exterior environmental condition value;
determining the optimal biometric condition value for the occupant associated with the sensed exterior environmental condition value;
comparing the optimal biometric condition value for the occupant to the sensed biometric condition value;
in response to a difference between the optimal biometric condition value and the sensed biometric condition value, generating a control signal to control an actuator to control the controllable interior environmental condition, wherein the control signal effectuates control of the actuator to reduce the difference between the sensed biometric condition value and the optimal biometric condition value;
receiving an occupant profile comprising a biometric condition value, interior environmental condition value, and external environmental condition value; and
dynamically modifying the occupant profile based on sensed biometric condition values, sensed interior environmental condition values, and sensed external environmental condition values, and generating a modified occupant profile comprising a biometric condition value, interior environmental condition value, and external environmental condition value.

19. The method of claim 18 wherein the biometric condition comprises at least one of cardiac activity, blood pressure, blood rheology, blood oxygenation, blood saturation, respiratory activity, temperature, perspiration, conductance, musculoskeletal activity, and brain waves, wherein the controllable interior environmental condition comprises at least one of a seat position, seat temperature, interior temperature, audio level, ventilation, heating setting, cooling setting, and lighting condition, and wherein the exterior environmental condition comprises at least one of a time of day, day of week, date, season, weather condition, light condition, travel destination, travel time, traffic density, road type, and topography.

20. A non-transitory computer readable storage medium having stored computer executable instructions for controlling an interior environmental condition in a vehicle comprising a biometric sensor to sense a biometric condition of an occupant of a vehicle seat and generate a signal representative of a value of the sensed biometric condition, a vehicle interior sensor to sense a controllable interior environmental condition in the vehicle and generate a signal representative of a value of the sensed interior environmental condition, a vehicle exterior sensor to sense an environmental condition exterior to the vehicle and generate a signal representative of a value of the sensed exterior environmental condition, wherein a controller is to receive the biometric condition signal, the interior environmental condition signal, and the exterior environmental condition signal, wherein each of a plurality of exterior environmental condition values has associated therewith a biometric condition value defined as an optimal biometric condition value for the occupant for the corresponding exterior environmental condition value, the computer executable instructions to cause the controller to:
determine the optimal biometric condition value for the occupant associated with the sensed exterior environmental condition value;
compare the optimal biometric condition value for the occupant to the sensed biometric condition value;
in response to a difference between the optimal biometric condition value and the sensed biometric condition value, generate a control signal to control an actuator to control the controllable interior environmental condition, wherein the control signal effectuates control of the actuator to reduce the difference between the sensed biometric condition value and the optimal biometric condition value;

receive an occupant profile comprising a biometric condition value, interior environmental condition value, and external environmental condition value; and dynamically modify the occupant profile based on sensed biometric condition values, sensed interior environmental condition values, and sensed external environmental condition values, and generate a modified occupant profile comprising a biometric condition value, interior environmental condition value, and external environmental condition value.

* * * * *

UNITED STATES PATENT AND TRADEMARK OFFICE
CERTIFICATE OF CORRECTION

| | |
|---|---|
| PATENT NO. | : 11,524,691 B2 |
| APPLICATION NO. | : 16/524865 |
| DATED | : December 13, 2022 |
| INVENTOR(S) | : David Gallagher et al. |

It is certified that error appears in the above-identified patent and that said Letters Patent is hereby corrected as shown below:

In the Claims

Column 14, Line 20, Claim 1:
After "wherein the controller is"
Delete "configured".

Signed and Sealed this
Fifth Day of March, 2024

Katherine Kelly Vidal
*Director of the United States Patent and Trademark Office*